United States Patent [19]

Askinazy

[11] Patent Number: 4,759,365
[45] Date of Patent: Jul. 26, 1988

[54] SPRING COIL WIRE DEVICE

[76] Inventor: Leo Askinazy, 300 Liberty Avenue, Brooklyn, N.Y. 11207

[21] Appl. No.: 30,617

[22] Filed: Mar. 27, 1987

[51] Int. Cl.$^4$ ................................................ A16F 5/08
[52] U.S. Cl. .................................................... 128/342
[58] Field of Search ................................ 128/341–343, 128/206.18; 604/94

[56] References Cited

U.S. PATENT DOCUMENTS

| 513,458 | 1/1894 | Dayton | 128/342 |
| 851,048 | 4/1907 | Woodward | 128/342 |
| 1,672,591 | 6/1928 | Wells | 128/342 |
| 4,201,201 | 5/1980 | Vergara | 128/342 X |
| 4,414,977 | 11/1983 | Rezakhany | 128/342 |

Primary Examiner—Tony M. Argenbright
Attorney, Agent, or Firm—Fleit, Jacobson, Cohn & Price

[57] ABSTRACT

A pair of barrel-shaped bodies are provided with each body constructed of resilient material and including a plurality of peripherally spaced and alternately oppositely axially end opening generally U-shaped body segments incorporating generally parallel legs interconnected at one pair of corresponding ends by an integral bight portion extending therebetween. The legs of peripherally adjacent and oppositely axially opening U-shaped body segments are at least substantially coextensive and are integrally formed.

9 Claims, 1 Drawing Sheet

SPRING COIL WIRE DEVICE

BACKGROUND OF THE INVENTION

1. Field of the Invention

This invention relates to a preformed wire device constructed of resilient material for use singly or in pairs and insertion into the anterior ends of a person's nasal passages, the wire devices serving to enlarge the anterior ends of the nasal passages and to possibly straighten a deviated septum, at least to some extent. Also, the invention may be used, possibly, in lieu of nose sprays to which a person has become addicted, at least until the addiction period has passed. Further, in instances of allergies, this device can be used for a short period and removed after allergic odors or substances have been cleared.

2. Description of Related Art

Various different forms of spring coil wire devices and nasal passage enlarging structures heretofore have been provided. Examples of such previously known devices are disclosed in U.S. Pat. Nos. 513,458, 851,048, 1,672,591, 4,201,201 and 4,414,977.

However, these previously known devices do not include the structural and operational features of the instant invention which enable the invention to perform the intended function in an improved manner.

SUMMARY OF THE INVENTION

A barrel-shaped body is provided wherein the body includes a plurality of peripherally spaced and alternately oppositely axial end opening generally U-shaped body segments incorporating generally parallel legs interconnected at one pair of corresponding ends by an integral bight portion extending therebetween. The legs of peripherally adjacent and oppositely axially opening U-shaped body segments are integrally formed and the body segments comprise wire-like members constructed of resilient material. One end of a barrel-like body is insertable into a nasal passage from the anterior end thereof and serves to enlarge that nasal passage anterior end by applying gentle outward pressure on those body portions defining the nasal passage anterior end, including the septum and the flesh portions of the nose opposite from the septum.

By enlarging one or both nasal passage anterior ends in this manner a deviated septum may be at least partially straightened and the anterior ends of the nasal passages are appreciably enlarged to facilitate the unrestricted flow of air therethrough during nasal breathing by a person having the spring-like barrel-shaped bodies inserted into their nasal passages. The increased flow of air enables many persons to breathe entirely through their nose (as opposed to through their mouth) and the additional flow of air through the nasal passages and into the sinus passages may comprise additional benefit if a person has allergies or a head cold in that a major portion of the nasal congestion which accompanies the common head cold may be evaporated and thus be prevented from collecting or compacting within the person's nasal and sinus cavities.

The main object of this invention is to provide a nasal passage insert which will facilitate a person breathing through his nasal passages as opposed to through his mouth, during both the waking hours and the sleeping hours.

Another object of this invention is to provide a nasal passage insert which will not only function to enlarge the anterior ends of the nasal passages of a person, but which will also function to at least partially straighten a deviated septum of a person utilizing the instant invention.

Another very important object of this invention is to provide a means for increasing the flow of air through nasal passages with a view toward evaporating nasal congestion caused by allergies or which usually accompanies a head cold to thereby substantially reduce the tendency of such congestion to collect and/or compact in a person's nasal and sinus cavities.

Still another object of this invention is to provide a nasal passage insert constructed in a manner which will limit the penetration of the insert into the nasal passages and enable the insert to be readily withdrawn from the nasal passages.

Another object of this invention is to provide a nasal passage insert constructed in a manner to facilitate the insertion of the insert into nasal passages.

A final object of this invention to be specifically enumerated herein is to provide a nasal passage insert in accordance with the preceding objects and which will conform to conventional forms of manufacture, be of simple construction and easy to use so as to provide a device that will be economically feasible, long lasting and relatively trouble free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

DESCRIPTION OF THE PREFERRED EMBODIMENT

Figure 1:
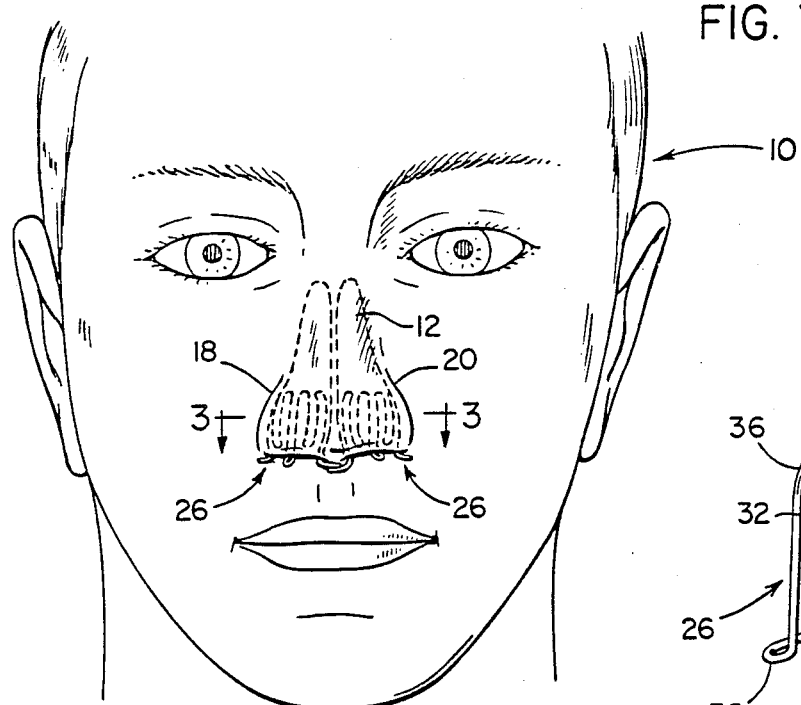
FIG. 1 is a fragmentary front elevational view of the head of a person and illustrating the manner in which the inserts of the instant invention may be supported within the anterior ends of a person's nasal passages.

Referring now more specifically to the drawings, the numeral 10 generally designates a human head including a nose 12. The nose 12 defines opposite side nasal passages 14 and 16 and a septum 17 separating the nasal passages 14 and 16.

Although the septum 17 defines the adjacent lateral limits of the passages 14 and 16, relatively pliant skin tissue portions 18 and 20 define the remote lateral limits of the passages 14 and 16.

In some persons the septum 17 will be deviated (including an intermediate length portion thereof which is laterally deflected to one side or the other) and in other cases the skin tissue portions 18 and 20 may have a contour such that the passages 14 and 16 are narrowed reasonably closely inward of the anterior ends 22 and 24 of the passages 14 and 16, either of which conditions can severely limit the amount of air which may be drawn inwardly through the passages 14 and 16. Persons who experience these difficulties must breathe through their mouths a majority of the time, at least when they are sleeping and a pillow or the bed surface acts to inwardly displace the tissue portion 14 or 16 disposed lowermost against the pillow or bed surface.

Such "mouth breathers" are subject to more throat infections, more rapid formation of tartar at the gum lines of their teeth and more nose and sinus cavity congestion during the periods they have head colds and/or allergies.

In order to alleviate these problems which reduce the amount of air which may be drawn inwardly through the passages 14 and 16 during normal breathing operations, a pair of spreaders referred to in general by the reference numerals 26 are provided. Each spreader 26 defines an open ended barrel-shaped body 28 constructed of resilient material and including a plurality of peripherally spaced and alternately opposite axial end opening generally U-shaped body segments 30 incorporating generally parallel legs 32 interconnected at one pair of corresponding ends by integral bight portions 34 extending therebetween. The legs of peripherally adjacent and oppositely axially opening U-shaped body segments are coextensive and integrally formed, the body segments 34 each being constructed of metallic wire-like material. Further, all of the body segments 30 are integrally formed from a single piece of wire and the ends of that single piece of wire may be fused together in any convenient location in order to form a continuous wire-type body. Also, with attention directed more specifically to FIG. 5, a modified form of spreader is referred to in general by the reference numeral 26' and includes a body 28' constructed of wire-like plastic material.

Figure 2:
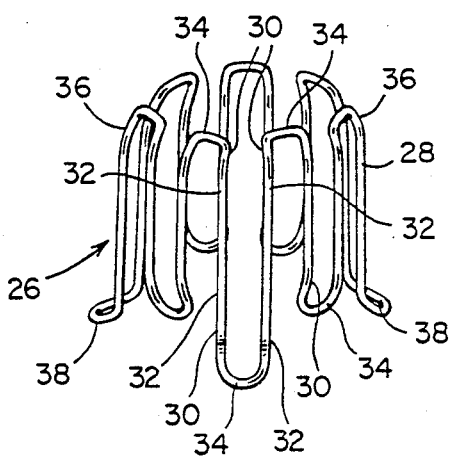
FIG. 2 is an enlarged perspective view of one of the inserts of the instant invention constructed of metal.
Figure 3:
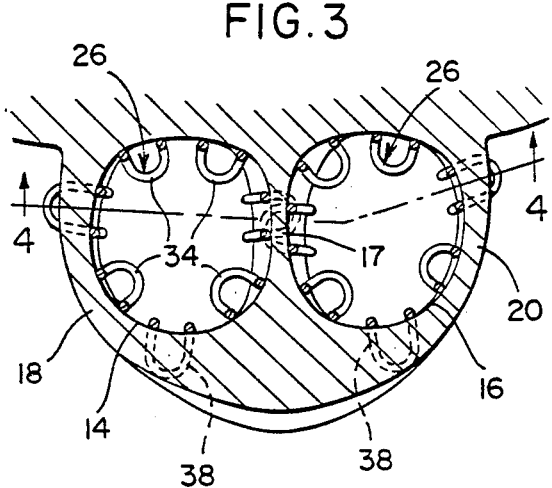
FIG. 3 is an enlarged fragmentary horizontal sectional view taken substantially upon the plane indicated by the section line 3—3 of FIG. 1.
Figure 4:
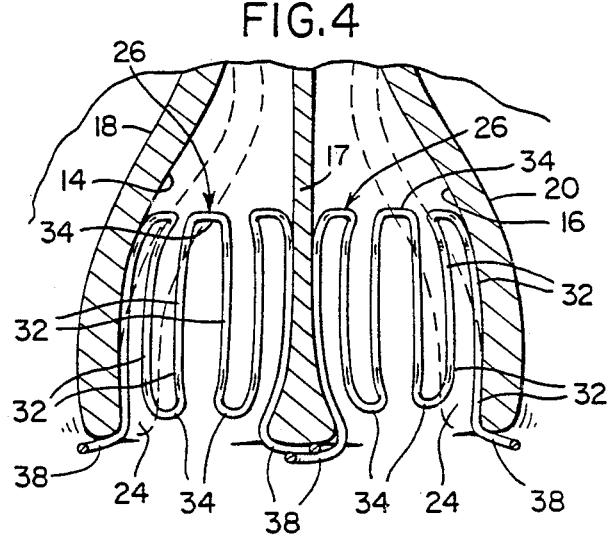
FIG. 4 is a fragmentary vertical sectional view taken substantially upon the plane indicated by the section line 4—4 of FIG. 3.

From FIGS. 2 and 4 of the drawings it may be seen that the bight portions 34 and adjacent leg ends of all of the body segments at one end of the body 28 are inwardly deflected as at 36. This facilitates the insertion of the corresponding end of the barrel-shaped body 28 or 28' into a nasal cavity from the anterior end thereof.

In addition, the bight portion 34 and adjacent legs of three body segments 30 at the other end of the barrel-shaped body 28 are outwardly deflected as at 38 and these segments including outwardly deflected bight portions are spaced generally 120° apart about the periphery of the barrel-shaped body 28. The body 28 includes, however, seven U-shaped body segments spaced about the end thereof including the outwardly deflected bight portions 34 with at least one body segment 30 having an inwardly deflected bight portion 34 and adjacent leg ends disposed between each pair of adjacent body segments 30 having outwardly deflected bight portions and adjacent leg ends. In fact, two body segments 30 with inwardly directed bight portions 34 are disposed between one pair of peripherally adjacent body segments 30 having out-turned bight portions 34. Therefore, the angular spacing between that one pair of body segments 30 with outwardly directed bight portions 34 is somewhat more than 120°.

Figure 5:
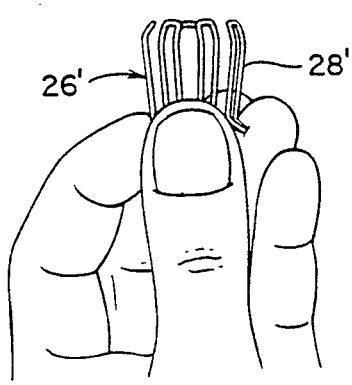
FIG. 5 is a perspective view of a modified form of insert constructed of plastic and illustrating the manner in which the insert may be held between the thumb and two fingers of a person's hand preparatory to insertion of the insert within a nasal passage and during removal of the insert from a nasal passage.

In operation, each body 28 is grasped in the manner illustrated in FIG. 5 by the thumb and two fingers of a person's hand with those two fingers and thumb each engaging one of the outwardly directed bight portions 34. In this manner, the body 28 may be comfortably and securely handled at one end and have the other end thereof carefully inserted into the anterior end of one of the nasal passages 14 and 16. After both bodies 28 have been inserted into the nasal passages 14 and 16 in the manner illustrated in FIG. 4, the tissue areas 18 and 20 will be outwardly displaced and any deviation in the anterior end of the septum 17 will be corrected, thus increasing the interior cross-sectional area of the passages 14 and 16 and facilitating the free flow of breathing air therethrough. By increasing the amount of air which may pass through the nose of a person experiencing nasal passage and sinus cavity congestion due to hay fever, allergies or a head cold, a considerable portion of the excess nasal and sinus cavity congestion may be evaporated. Further, by enabling a person to breathe through his or her nose as opposed to only through his or her mouth, throat irritations (which sometimes lead to head colds) and rapid tartar buildup on the teeth is reduced.

In many instances, as a result of trial usage of the spreaders 26, it has been found that temporary usage of the spreaders 26 will restore nasal breathing to such an extent that some period of time must lapse before hay fever or head cold congestion in the nasal passages and sinus cavities returns to such an extent that breathing through the nasal passages is impaired once the spreaders 26 are removed. Accordingly, it has been found that usage of the spreaders 26 for a short time upon arising may be sufficient to clear the head of nasal passage and sinus passage congestion for a significant period of time. Of course, the reduction of nasal passage and sinus cavity congestion often results in a head cold running its course in a considerably shorter period of time.

The out-turned bight portions 34 and adjacent leg ends define abutments for limiting insertion of the bodies 28 into the nasal passages 14 and 16 and further provide gripping surfaces by which the bodies 28 may be gripped in the manner illustrated in FIG. 5 of the drawings when it is desired to remove the spreaders 26.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A pair of spreaders for functioning to temporarily enlarge a person's nasal passages at the anterior ends thereof and also for functioning to temporarily straighten a deviated septum, said spreaders each including an open ended barrel-shaped body constructed of resilient material and wherein each body includes a plurality of peripherally spaced and alternately opposite axial end opening generally U-shaped body segments incorporating generally parallel legs interconnected at one pair of ends by an integral bight portion extending therebetween and further wherein the legs of peripherally adjacent and oppositely axially opening U-shaped body segments are integrally formed.

2. The spreaders of claim 1 wherein the body segments of each body are constructed of wire-like material.

3. The spreaders of claim 2 wherein said material comprises a metal which is inert in its working environment.

4. The spreaders of claim 2 wherein said material comprises a plastic which is inert in its working environment.

5. The spreaders of claim 1 wherein said bight portions and the adjacent ends of the corresponding legs at one end of said barrel-shaped body are inwardly deflected.

6. The spreaders of claim 5 wherein the U-shaped body segments at the other end of said barrel-shaped body equal at least six in number and the bight portions and adjacent leg ends of generally equally peripherally spaced U-shaped body segments at said other end of said body are outwardly directed.

7. The spreaders of claim 6 wherein the bight portions of the other U-shaped body segment at said other end of said barrel-shaped body and the adjacent leg ends are inwardly directed.

8. The spreaders of claim 7 wherein the body segments of each body are constructed of wire-like material.

9. A spreader for functioning to enlarge the interior transverse dimensions of a passage portion circumferentially bound by resilient passage wall portions and for lengthwise insertion into said passage portion, said spreader including an open ended barrel-shaped body constructed of resilient material, said body including a plurality of peripherally spaced apart and alternately opposite axial end opening generally U-shaped body segments each incorporating generally parallel legs interconnected at one pair of ends by an integral bight portion extending therebetween and further wherein the legs of peripherally adjacent and opositely axially opening U-shaped body segments are integrally formed.

* * * * *